United States Patent
Kargar et al.

(10) Patent No.: US 8,224,129 B2
(45) Date of Patent: Jul. 17, 2012

(54) AUTO-DELETION OF IMAGE RELATED DATA IN AN IMAGING SYSTEM

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 584 days.

(21) Appl. No.: 12/495,021

(22) Filed: Jun. 30, 2009

(65) Prior Publication Data
US 2010/0002919 A1    Jan. 7, 2010

Related U.S. Application Data

(60) Provisional application No. 61/077,195, filed on Jul. 1, 2008.

(51) Int. Cl.
*G06K 9/00* (2006.01)
*G06K 9/60* (2006.01)

(52) U.S. Cl. ........................................ 382/305; 382/128
(58) Field of Classification Search ............... 382/305, 382/128
See application file for complete search history.

(56) References Cited

U.S. PATENT DOCUMENTS

| | | | | |
|---|---|---|---|---|
| 4,958,283 A | * | 9/1990 | Tawara et al. | 382/131 |
| 5,715,823 A | * | 2/1998 | Wood et al. | 600/437 |
| 6,253,214 B1 | * | 6/2001 | Hall et al. | 707/667 |
| 6,445,460 B1 | * | 9/2002 | Pavley | 358/1.15 |
| 6,820,100 B2 | * | 11/2004 | Funahashi | 1/1 |
| 7,259,729 B2 | * | 8/2007 | Shastri et al. | 345/1.3 |
| 7,310,651 B2 | * | 12/2007 | Dave et al. | 705/3 |
| 2006/0083442 A1 | * | 4/2006 | Loukipoudis et al. | 382/305 |
| 2008/0177808 A1 | * | 7/2008 | Raghavan | 707/204 |

OTHER PUBLICATIONS

A W Wong, H K Huang, R L Arenson and J K Lee "Digital archive system for radiologic images" RadioGraphics vol. 14, No. 5, 1994, pp. 1119-1126.*

* cited by examiner

*Primary Examiner* — Bhavesh Mehta
*Assistant Examiner* — Utpal Shah
(74) *Attorney, Agent, or Firm* — Alexander J Burke

(57) ABSTRACT

A system for auto-deletion of image related data in an imaging system, includes an imaging system. The imaging system comprises a repository for storing image representative data, and is capable of archiving image representative data in the repository, and deleting image representative data from the repository. The system also includes an archiving system, coupled to the imaging system, for receiving image representative data from the imaging system and archiving the received data. The imaging system automatically deletes image representative data which has been archived from the repository.

14 Claims, 1 Drawing Sheet

AUTO-DELETION OF IMAGE RELATED DATA IN AN IMAGING SYSTEM

The present invention is a non-provisional application based on provisional application No. 61/077,195, filed Jul. 1, 2008 by S. Kargar et al.

FIELD OF THE INVENTION

The present invention relates to an imaging system coupled to an archiving system, and in particular to a medical imaging system including the capability of storing data representing a plurality of images associated with a patient examination, and for archiving data representing images from the medical imaging system in the archiving system.

BACKGROUND OF THE INVENTION

Medical imaging systems, including X-ray, ultrasound, magnetic resonance, positron emission tomography, computed tomography, endoscopy, mammography, digital radiography, computed radiography and angiography systems, currently use digital imaging technology to generate and store data representing images in a repository. For example, during a patient examination, one or more images related to the examination are taken of an area of interest in the patient. Image representative data is stored in the repository in the imaging system. This image representative data is retrieved and displayed as an image for review by medical personnel.

Due to limited storage capacity of the repository in the imaging system, however, eventually the repository becomes full or near full. In this situation, some image representative data needs to be removed from the repository to make room for new data. To free up storage capacity in the imaging system, the imaging system provides the capability to delete data representing images or groups of images, for example, data representing a group of images related to a patient examination. A user of the imaging system employs a user interface to designate an image, a group of images, or the images related to a patient examination to be deleted from the repository of the imaging system. However, it is desired, or in some cases required, to preserve the image representative data.

Archiving systems have been developed which allow imaging systems to copy image representative data from the imaging system to the archiving system. One type of such archiving systems is termed Picture Archiving and Communications Systems (PACS). In medical imaging, PACS are computers or networks dedicated to the storage, retrieval, distribution and presentation of images. They typically are located remote from the health care facility where the imaging system is located, and provide for replacement for hard copies of the image representative data, long term secure storage of electronic copies of image representative data, and remote access to the image representative data. The medical images in the PACS are stored in an independent format. The typical format for image storage is Digital Imaging and Communications in Medicine (DICOM) format. A user controls the imaging system to archive image representative data in the imaging system.

However, after the image representative data in the imaging system has been archived to the PACS, that data still remains in the repository in the imaging system. After archiving, if desired, a user manually deletes the images from the imaging system, in the manner described above, to free the space in the repository. This manual process is time consuming and subject to errors. For example, a user employs an image browser, which is a GUI, to locate the desired images. When there are many images in the repository, this can take a significant amount of time. The user also needs to properly designate the desired images to delete. A user may mistakenly delete images which should be kept, or may not delete images which should be deleted. The former results in desired images which are not available for review when requested; the latter results in storage space in the repository which is not freed.

A system which will automatically delete image representative data from an imaging system after it has been archived is desirable. Such a system will minimize errors in deletion of image representative data in the imaging system and facilitates search for images in the imaging system. By automatically deleting archived images it is unnecessary for a user to sort through them when looking for a desired image or group of images.

BRIEF DESCRIPTION OF THE INVENTION

In accordance with principles of the present invention, a system provides auto-deletion of image related data in an imaging system. The imaging system comprises a repository for storing image representative data, and is capable of archiving image representative data in the repository, and deleting image representative data from the repository. The system also includes an archiving system, coupled to the imaging system, for receiving image representative data from the imaging system and archiving the received data. The imaging system further automatically deletes image representative data which has been archived from the repository.

DETAILED DESCRIPTION

Figure 1:
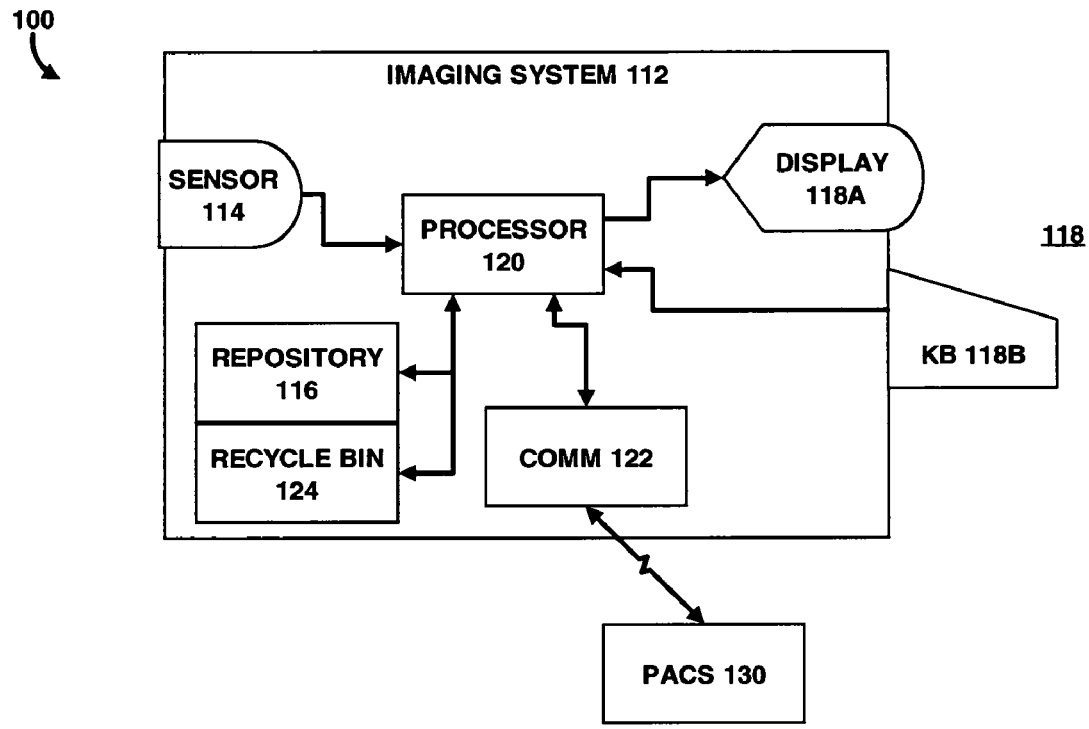
FIG. 1 is a block diagram of a system for auto-deletion of image related data in an imaging system according to the present invention.

A processor, as used herein, is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, imaging system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by the display processor under the control of the processor. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to the processor. The processor, under control of the executable procedure or executable application manipulates the UI display images in response to the signals received from the input devices. In this way, the user interacts with the display image using the input devices, enabling user interaction with the processor or other device. A graphical user interface (GUI) uses graphical display images, as opposed to textual display images, when generating the UI.

A form, as used herein, is a type of UI display image. A form UI display image includes display elements, such as textual display, which prompt the user to enter particular information; and display elements, such as text boxes, check boxes etc., into which the user, using the input devices, may enter the particular information. A form may also include elements which permit a user to pass commands and/or requests to the processor, such as push buttons, or menu items.

FIG. 1 is a block diagram of a system 100 according to the present invention. In general, a system 100 for auto-deletion of image related data in an imaging system includes an imaging system 112. The imaging system 112 includes a repository 116 for storing image representative data. The imaging system 112 is capable of archiving image representative data in the repository 116, and deleting image representative data from the repository 116. An archiving system 130, which in FIG. 1 is a picture archiving and communications system (PACS), is coupled to the imaging system 112, receives image representative data from the imaging system 112, and archives the received data. The imaging system 112 automatically deletes image representative data which has been archived from the repository 116.

Figure 2:
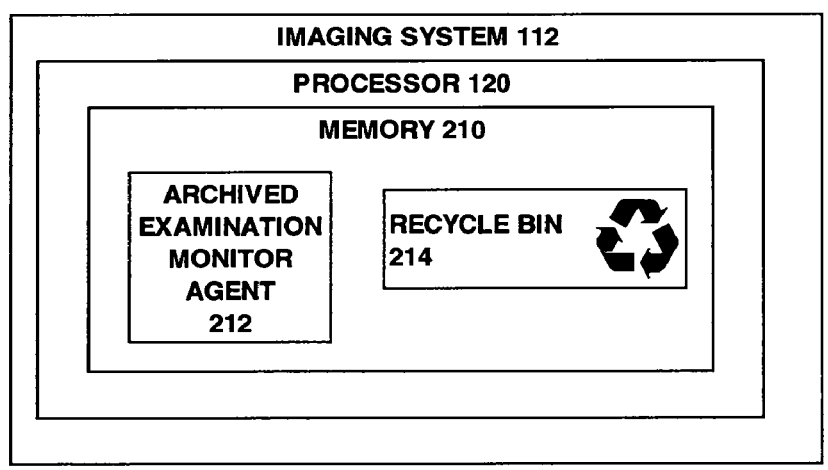
FIG. 2 is a memory layout diagram implementing one embodiment of the system according to the present invention.

More specifically, the imaging system 112 relates data representing one or more images to a patient examination and the image representative data is accessed by reference to the related patient examination. The imaging system 112 also includes a processor 120 which executes an executable procedure for traversing the respective patient examinations in the repository 116 to determine whether to delete the image representative data related to the patient examination, and if so, to delete the image representative data related to the patient examination. FIG. 2 is a memory layout diagram of memory in the processor 120 according to the present invention. In FIG. 2, the imaging system 112 includes an executable procedure 212, termed an archived examination monitor agent (AEMA), for traversing the respective patient examinations, and an executable procedure 214 for implementing a recycle bin 124 (described below). The executable procedure 212 (AEMA) for traversing the respective patient examinations determines whether to delete image representative data related to the patient examination based on data in the database, including Meta data. For example. the AEMA 212 may determine whether to delete image representative data related to the patient examination based on at least one of: (a) whether the image representative data related to the patient examination has been archived, (b) whether the archiving system 130 has acknowledged successful archiving of the image representative data related to the patient examination, (c) the examination date, (d) whether the patient examination and/or related image representative data are flagged as protected by the user, (e) whether the patient has a scheduled follow-up procedure set by the hospital information system, (f) whether the patient examination study is closed, (g) whether the examination study report is signed off by the physician, (h) whether the patient has been discharged, (i) whether the patient has been transferred, and (j) whether the used space in the mass storage device containing the repository 116 reaches a predetermined value. More specifically, as one example, the executable procedure 212 (AEMA) for traversing the respective patient examinations determines to delete image representative data related to the patient examination when: (a) the image representative data related to the patient examination has been archived, (b) the archiving system 130 has acknowledged successful archiving of the image representative data related to the patient examination, and (c) the examination date is earlier than a specified date.

In one embodiment, the imaging system 112 automatically stores a copy of the image representative data to a recycle bin 124 before it deletes image representative data which has been archived from the repository 116. Specifically, the executable procedure 212 (AEMA) stores a copy of the image representative data related to a patient examination determined to be deleted to the recycle bin 124 before deleting the image representative data related to the patient examination.

In one implementation, the imaging system 112 is a medical imaging system. More specifically, the imaging system 112 is one of: an X-ray, ultrasound, magnetic resonance, positron emission tomography, computed tomography, endoscopy, mammography, digital radiography, computed radiography, and angiography imaging system.

In general operation, the system 100 for auto-deletion of image related data in an imaging system 112 stores image representative data in the repository 116 in the imaging system 112. The imaging system 112 is operated to archive image representative information in the repository 116 in an archiving system 130. The archived image representative data is automatically deleted from the repository 116 in the imaging system 112. More specifically, data representing one or more images is related to a patient examination and the image representative data is accessed by reference to the patient examination. The respective patient examinations in the repository 116 are traversed to determine whether to delete the image representative data related to the patient examination. If so, the image representative data related to the patient examination is deleted. Determining whether to delete the image representative data related to the patient examination is based on at least one of: (a) whether the image representative data related to the patient examination has been archived, (b) whether the archiving system 130 acknowledges successful archiving of the image representative data related to the patient examination, and (c) the examination date. More specifically, image representative data related to a patient examination is determined to be deleted when: (a) the image representative data related to the patient examination has been archived, (b) the archiving system 130 has acknowledged successful archiving of the image representative data related to the patient examination, and (c) the patient examination date is earlier than a specified date. In one embodiment, before the image representative data from the repository 116 in the imaging system 112 is automatically deleted, a copy of the image representative data from the repository 116 is automatically stored in the recycle bin 124.

Described in more detail, in FIG. 1, an imaging system 112 generates data representing one or more images related to a patient examination. In the embodiment illustrated in FIG. 1, the imaging system 112 is an angiography imaging system for generating images representing blood vessels within a patient. The imaging system 112 includes a sensor 114 which generates data representing a physiological characteristic of the patient. In this case, the data represents an image of blood vessels in the patient. An output terminal of the sensor 114 is coupled to an input terminal of a processor 120. A bidirectional terminal of the processor 120 is coupled to respective corresponding terminals of a repository 116 and a recycle bin 124. The repository 116 and recycle bin 124 are a non-volatile storage media, and may be implemented as a hard disk drive, a CD/ROM and/or a DVD storage medium, or any other appropriate mass storage device. Although illustrated as sharing a single mass storage device in FIG. 1, one skilled in the art understands that they may be implemented in separate mass storage devices. A second bidirectional terminal of the processor 120 is coupled to a corresponding terminal of a communications port 122.

A graphical user interface (GUI) 118 consists of a display device 118A and a user input device 118B. An output terminal of the processor 120 is coupled to an input terminal of the display device 118A and an input terminal of the processor 120 is coupled to an output terminal of the user input device 118B. The imaging system 112 is in communication with an archiving system 130, which in the illustrated embodiment is a picture archiving and communications system (PACS), via the communications port 122. The communications port 122 and PACS 130 may communicate through any appropriate data communications channel using an appropriate communications protocol. For example, as described above, the PACS 130 may be located remote from the imaging system 112. In such an arrangement, the imaging system 112 may communicate with the PACS 130 using a wide area network (WAN) such as the Internet using the TCP/IP protocol in a known manner. Additional known security measures may be employed as well.

In operation, data related to an examination is stored in the repository 116. The examination related data may be stored on the repository 116 mass storage device as a database in any of many known forms, such as Microsoft Access®, SQL, Oracle®, SyBase®, and so forth. The data stored in the repository 116 database includes the image representative data along with additional data associated with the examination and/or images, sometimes termed Meta data. Meta data may include, for example: the patient name; the doctor name; an identifier for the examination; other information about the examination, such as the type of examination, the area of the patient body, parameters such as X-ray strength, contrast agent, and so forth. Meta data parameters advantageously include: (a) whether the image representative data related to the patient examination has been archived, (b) whether the archiving system 130 has acknowledged successful archiving of the image representative data related to the patient examination, (c) the examination date, (d) whether the patient examination and/or related image representative data are flagged as protected by the user, (e) whether the patient has a scheduled follow-up procedure set by the hospital information system, (f) whether the patient examination study is closed, (g) whether the examination study report is signed off by the physician, (h) whether the patient has been discharged, (i) whether the patient has been transferred, and (j) whether the used space in the mass storage device containing the repository 116 reaches a predetermined value.

The processor 120 interacts with a user via the user interface 118. The display device 118A presents data to the user and the user input device 118B receives data from the user. Using the user interface 118, a user may designate an examination and/or images related to an examination to be archived. To do this, the user searches for the desired examination, using the user interface 118, then issues a command to archive the data related to that examination. In the present embodiment, the user interface 118 may be a graphical user interface (GUI) which presents a search form to the user. Such search forms are well known, are not germane to the present invention and are not illustrated. One skilled in the art understands how to generate such a form and use such a form to receive search parameters from the user via the GUI 118.

The processor 120 uses the received search parameters to search the database containing the examination representative data. The processor 120 forms a query from the search parameters and applies that query to the database to extract those examination records which match the search parameters. The various database formats have their own query languages, including, for example, SQL language, XQuery, etc. One skilled in the art knows how to generate a search query in the appropriate query language from the received search parameters and how to execute that search on the database. The result of the search is a list of retrieved examination records matching the search criteria. Data representing the retrieved records are displayed on the display device 118A. The user then selects one or more desired examinations, and issues an archive command. This may be done by including a GUI element, such as a push button or menu selection item, which, when activated, initiates archiving the examination related image data. One skilled in the art understands how to design, construct and operate such a GUI.

In response to receipt of an archive command, the processor 120 communicates with the PACS 130 via the communications port 122 and arranges for a transaction in which data representing the specified examination or examinations, and the related images, is archived. A copy of data representing the examination (including Meta data and image representative data) is transferred to the PACS 130. The PACS 130, in turn, sends an acknowledgment message back to the imaging system 112 to indicate that all data has been successfully received, stored and verified. The processor 120 receives the acknowledgment message and, for each archived examination, updates the Meta data examination status (described above) to indicate that this examination has been archived; and updates the Meta data storage commitment (also described above) to indicate receipt of an acknowledgment message from the PACS 130.

The imaging system 120 further includes executable procedures to automatically delete archived examination representative data from the repository 116. FIG. 2 is a memory layout diagram implementing one embodiment of the system 100 according to the present invention. In FIG. 2, the imaging system 112 is illustrated as including the processor 120 which, in turn contains a memory 210. The memory 210 is accessible by the processor 120, and is used to store data representing executable applications, executable procedures, and data in a known manner. One skilled in the art understands that the memory 210 may be a combination of read-only memory (ROM) and/or read-write memory (RAM); may be a combination of volatile and/or non-volatile memory; and may use any technology of memory which is appropriate for use with the processor 120. In FIG. 2, the memory 210 includes data representing an executable procedure for implementing an archived examination monitor agent 212, and data representing an executable procedure 214 for implementing a recycle bin 124. The recycle bin 124 is a second storage area capable of holding data representing examinations, including image representative data. Examination data in the recycle bin 124 is not available through the repository 116, and does not appear in an examination list or search of the data in the repository 116. The recycle bin 124 may be implemented on the same mass storage device as the repository 116, i.e. the same hard disk drive, as illustrated in FIG. 1; or may be implemented on a different mass storage device.

The archived examination monitor agent (AEMA) 212 monitors the examinations stored in the repository 116 (FIG. 1). More specifically, it evaluates the respective patient examinations in the repository 116. This may happen periodically, continually, or in response to a trigger. For example, the AEMA 212 may traverse the respective patient examinations stored in the repository 116, then wait for a period of time and repeat the action. Alternatively, the AEMA 212 may traverse the respective patient examinations in the repository 116 and start again immediately after it is finished, or may receive a trigger signal (e.g. once per hour) from another executable procedure to trigger it to traverse the examination data in the repository 116.

As the AEMA 212 traverses the respective patient examinations in the repository 116 (FIG. 1), it evaluates the Meta data associated with the examination to determine if the data related to this examination should be deleted. As described above, in one embodiment, items of Meta data employed for evaluation by the AEMA 212 include: (a) the examination status (has the examination data been archived); (b) the storage commitment (has an acknowledgment been received from the PACS 130); and (c) the examination date. For example, the AEMA 212 may delete examination data which has been archived, or which has been archived and for which an acknowledgment has been received from the PACS 130. Alternatively, examinations which are older than a predetermined date, which may specified either as an absolute date (i.e. Apr. 26, 2008) or as a relative date (i.e. older than 6 months), may be deleted. A combination of these criteria may also be specified: e.g. delete examination data which (a) has been archived, and (b) acknowledgment received, and (c) which is earlier than a specified date, i.e. earlier than 6 months. One skilled in the art understands that other Meta data may also be included in the predetermined criteria used by the AEMA 212 to determine which examination related data to delete.

As the AEMA 212 traverses the respective patient examinations in the repository 116 (FIG. 1), if the related Meta data meets the criteria (e.g. it is archived, acknowledgment received and is older than 6 months old) that data is deleted from the repository 116. The examination representative data may be deleted from the repository 116 outright. In this embodiment, once the examination representative data has been deleted, it becomes unavailable to the user of the imaging device 112. If required, it may be retrieved from the PACS 130 in a known manner.

However, in a preferred embodiment, the examination representative data identified by the AEMA 212 is removed from the repository 116 and stored in another storage area known as recycle bin 124 by an executable procedure in AEMA 212. In this embodiment, the examination representative data remains available to the imaging system 112 by accessing the recycle bin 214. However, the examination representative data is not stored in the repository 116 and is not listed in a list or in search results of examinations contained in the repository 116.

The AEMA 212 also monitors the status of the recycle bin 124 and/or the mass storage device implementing the recycle bin 124 and repository 116 (FIG. 1). When the used space on the mass storage device implementing the recycle bin 124 reaches a predetermined space limit, a warning message is issued warning that space in the recycle bin 124 is close to being filled and an administrator should free some space by deleting some examination representative data from the recycle bin 124. Similarly, when the used space on the mass storage device implementing the recycle bin 124 reaches a predetermined maximum, an error message is issued to alert an administrator that space in the recycle bin 214 is completely filled and needs to be freed. In the case of the recycle bin 124, when examination data is removed, it is permanently removed.

A system according to the present invention minimizes human errors occurring when manually deleting archived examination representative data from the repository 116 of the imaging system 112. This results in maximizing the amount of storage space available in the repository 116 while minimizing the chance that required examination data are inadvertently removed. It also speeds searches of the repository 116 by automatically removing records of examinations which have been archived from the repository 116.

The present invention has been described in terms of a medical imaging system, and particularly in terms of an angiography imaging system. One skilled in the art understands that any imaging system containing a repository and using an archiving system may benefit from the advantageous operation of an automatic deletion system according to the present invention, as described above. One skilled in the art also understands that other arrangements of hardware and software may be used to accomplish the functions of the present invention described above. For example, the AEMA 212 executable procedure and recycle bin 214 executable procedure (of FIG. 2) may be combined into a single executable procedure providing the functionality of the AEMA 212 and recycle bin 124.

What is claimed is:

1. A system for auto-deletion of image related data in an imaging system, comprising:
   an imaging system, comprising a repository for storing image representative data, capable of archiving image representative data in the repository, and deleting image representative data from the repository; and
   an archiving system, coupled to the imaging system, for receiving image representative data from the imaging system and archiving the received data; wherein:
   the imaging system automatically deletes image representative data which has been archived from the repository and the imaging system automatically stores a copy of the image representative data to non-volatile storage media before it deletes image representative data which has been archived from the repository.

2. The system of claim 1, wherein said non-volatile storage media comprises a recycle bin and the imaging system relates data representing one or more images to a patient examination and the image representative data is accessed by reference to the related patient examination.

3. The system of claim 2, wherein the imaging system further comprises a processor executing an executable procedure for traversing the respective patient examinations in the repository to determine whether to delete the image representative data related to the patient examination, and if so, to delete the image representative data related to the patient examination.

4. The system of claim 3, wherein the executable procedure for traversing the respective patient examinations determines whether to delete image representative data related to the patient examination based on at least one of: (a) whether the image representative data related to the patient examination has been archived, (b) whether the archiving system has acknowledged successful archiving of the image representative data related to the patient examination, (c) the examination date, (d) whether the patient examination and/or related image representative data are flagged as protected by a user, (e) whether the patient has a scheduled follow-up procedure set by the hospital information system, (f) whether the patient examination study is closed, (g) whether the examination study report is signed off by the physician, (h) whether the patient has been discharged, (i) whether the patient has been transferred, and (j) whether the used space in the mass storage device containing the repository reaches a predetermined value.

5. The system of claim 4, wherein the executable procedure for traversing the respective patient examinations determines that image representative data related to a patient examination is to be deleted when: (a) the image representative data related to the patient examination has been archived, (b) the archiving system has acknowledged successful archiving of the image representative data related to the patient examination, and (c) the patient examination date is earlier than a specified date.

6. The system of claim 1, wherein the imaging system is a medical imaging system.

7. The system of claim 6, wherein the imaging system is one of an X-ray, ultrasound, magnetic resonance, positron emission tomography, computed tomography, endoscopy, mammography, digital radiography, computed radiography, and angiography imaging system.

8. A system for auto-deletion of image related data in an imaging system, comprising:
an imaging system, comprising a repository for storing image representative data, capable of archiving image representative data in the repository, and deleting image representative data from the repository; and
an archiving system, coupled to the imaging system, for receiving image representative data from the imaging system and archiving the received data; wherein:
the imaging system automatically deletes image representative data which has been archived from the repository wherein the imaging system automatically stores a copy of the image representative data to a recycle bin before it deletes image representative data which has been archived from the repository.

9. The system of claim 8, wherein the imaging system further comprises:
an executable procedure for implementing a recycle bin; and
the executable procedure for traversing the respective patient examinations stores a copy of the image representative data related to a patient examination determined to be deleted to the recycle bin before deleting the image representative data related to the patient examination.

10. A method for operating a system for auto-deletion of image related data in an imaging system, comprising the steps of:
storing image representative data in a repository in the imaging system;
operating the imaging system to archive said image representative information in the repository in an archiving system; and
automatically deleting the archived image representative data from the repository in the imaging system and the imaging system automatically stores a copy of the image representative data to non-volatile storage media before it deletes image representative data which has been archived from the repository.

11. The method of claim 10, wherein:
the step of storing image representative data in the repository comprises the step of relating data representing one or more images to a patient examination and accessing the image representative data by reference to a patient examination; and
the step of automatically deleting image representative comprises the step of traversing the respective patient examinations in the repository to determine whether to delete the image representative data related to the patient examination, and if so to delete the image representative data related to the patient examination.

12. The method of claim 11, wherein the step of determining whether to delete the image representative data related to the patient examination is based on at least one of: (a) whether the image representative data related to the patient examination has been archived, (b) whether the archiving system 130 has acknowledged successful archiving of the image representative data related to the patient examination, (c) the examination date, (d) whether the patient examination and/or related image representative data are flagged as protected by the user, (e) whether the patient has a scheduled follow-up procedure set by the hospital information system, (t) whether the patient examination study is closed, (g) whether the examination study report is signed off by the physician, (h) whether the patient has been discharged, (i) whether the patient has been transferred, and (j) whether the used space in a storage device reaches a predetermined value.

13. The system of claim 12, wherein the step of determining whether to delete the image representative data related to a patient examination comprises the step of determining to delete image representative data related to a patient examination when: (a) the image representative data related to the patient examination has been archived, (b) the archiving system has acknowledged successful archiving of the image representative data related to the patient examination, and (c) the patient examination date is earlier than a specified date.

14. A method for operating a system for auto-deletion of image related data in an imaging system, comprising the steps of:
storing image representative data in a repository in the imaging system;
operating the imaging system to archive said image representative information in the repository in an archiving system;
automatically deleting the archived image representative data from the repository in the imaging system, wherein before the step of automatically deleting the image representative data from the repository in the imaging system, the step of automatically storing a copy of the image representative data from the repository in a recycle bin.

* * * * *